US 6,950,761 B2

(12) United States Patent
Ramanujachar

(10) Patent No.: US 6,950,761 B2
(45) Date of Patent: Sep. 27, 2005

(54) WAVELET ANALYSIS OF ONE OR MORE ACOUSTIC SIGNALS TO IDENTIFY ONE OR MORE ANOMALIES IN AN OBJECT

(75) Inventor: Kartik Ramanujachar, Sugarland, TX (US)

(73) Assignee: Texas Instruments Incorporated, Dallas, TX (US)

( * ) Notice: Subject to any disclaimer, the term of this patent is extended or adjusted under 35 U.S.C. 154(b) by 85 days.

(21) Appl. No.: 10/749,886

(22) Filed: Dec. 31, 2003

(65) Prior Publication Data

US 2005/0021263 A1 Jan. 27, 2005

Related U.S. Application Data

(60) Provisional application No. 60/486,663, filed on Jul. 11, 2003.

(51) Int. Cl.$^7$ .............................. G01F 1/00; G01F 7/00; G06F 19/00
(52) U.S. Cl. ........................... 702/48; 702/66; 702/159; 702/189
(58) Field of Search .............................. 702/17, 35, 39, 702/57–59, 66, 71, 159, 189; 73/659; 367/38, 131, 104; 324/637, 639, 642

(56) References Cited

U.S. PATENT DOCUMENTS

| 4,924,449 | A | * | 5/1990 | Guigne ........................ 367/104 |
| 5,243,565 | A | * | 9/1993 | Yamamoto .................... 367/131 |
| 5,740,036 | A | * | 4/1998 | Ahuja et al. .................. 702/17 |
| 2004/0230383 | A1 | * | 11/2004 | Bechhoefer et al. .......... 702/57 |
| 2005/0021256 | A1 | * | 1/2005 | Wills et al. .................... 702/66 |
| 2005/0021257 | A1 | * | 1/2005 | Wills et al. .................... 702/66 |

OTHER PUBLICATIONS

Michael Dockins, Texas Instruments, Inc., "Frequency Domain Analysis of Time Domain Reflectometry Signals," Aug. 9, 2002, 43 pages, Aug. 2, 2002.
Michael Dockins, "Affidavit of Michael D. Dockins," signed Jan. 15, 2004, 2 pages, Jan. 15, 2004.

* cited by examiner

Primary Examiner—John Barlow
Assistant Examiner—Aditya Bhat
(74) Attorney, Agent, or Firm—Yingsheng Tung; Wade James Brady, III; Frederick J. Telecky, Jr.

(57) ABSTRACT

In one embodiment, a method for wavelet analysis of one or more acoustic signals to identify one or more anomalies in an object includes receiving an acoustic signal from an acoustic scan of an object and calculating a wavelet power spectrum of the acoustic signal. The method also includes accessing a library of one or more reference wavelet power spectra that each correspond to one or more objects that comprise one or more known anomalies and comparing the wavelet power spectrum with one or more reference wavelet power spectra. If the wavelet power spectrum from the acoustic scan corresponds to one or more reference wavelet power spectra, analysis results are communicated indicating that the object under analysis comprises one or more particular known anomalies corresponding to the one or more reference wavelet power spectra that correspond to the wavelet power spectrum. If the wavelet power spectrum does not correspond to one or more reference wavelet power spectra, analysis results are communicated indicating that the object under analysis lacks the one or more known anomalies that the one or more reference wavelet power spectra in the library correspond to.

19 Claims, 4 Drawing Sheets

*FIG. 4*
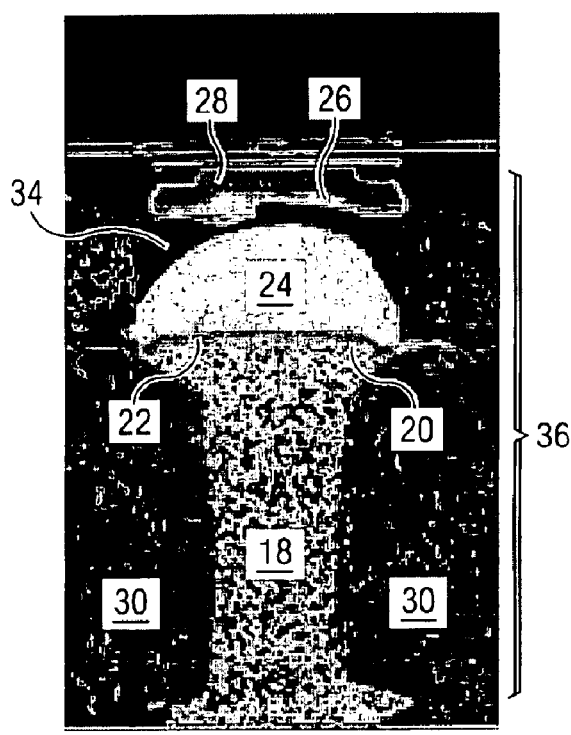
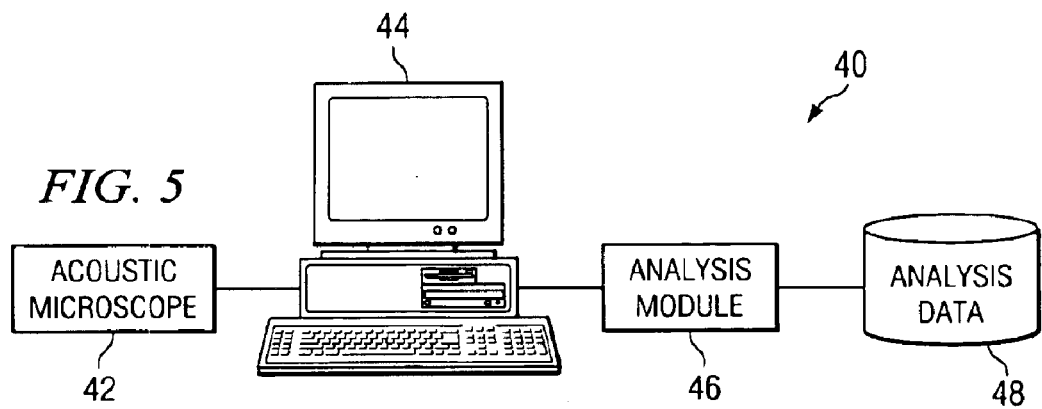
*FIG. 5*

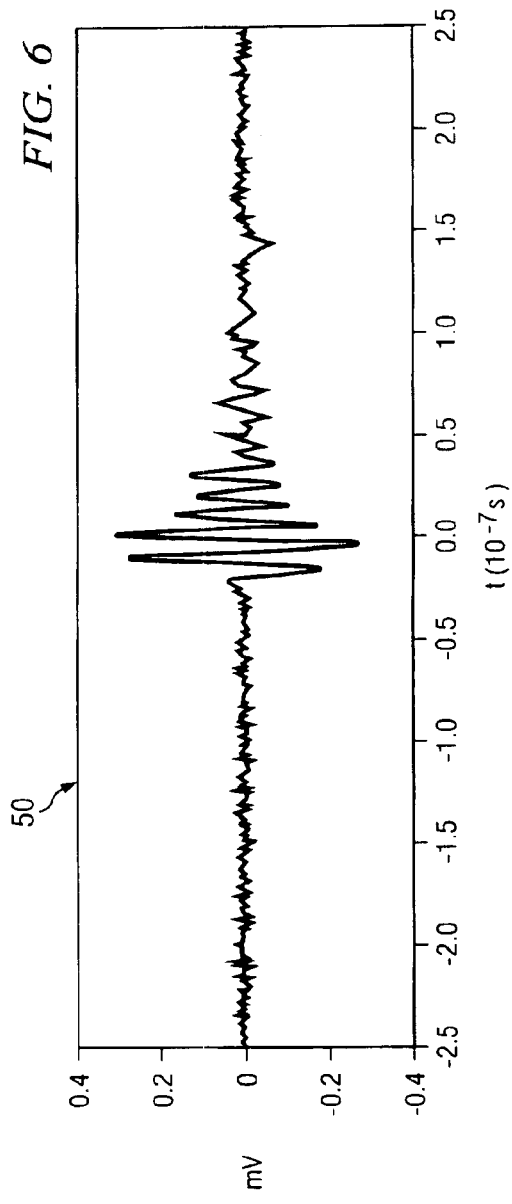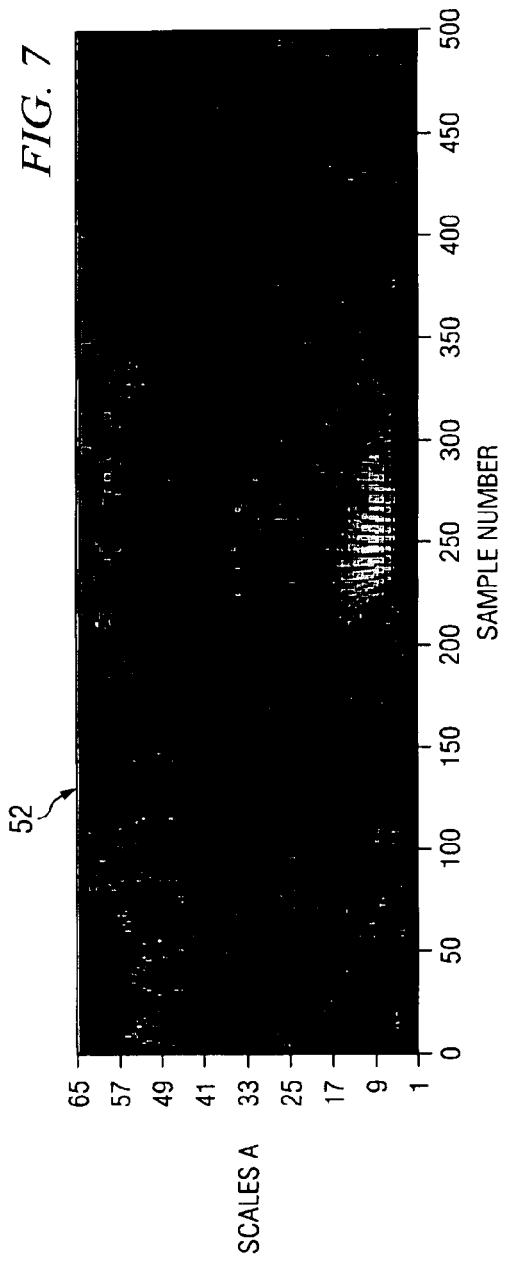

WAVELET ANALYSIS OF ONE OR MORE ACOUSTIC SIGNALS TO IDENTIFY ONE OR MORE ANOMALIES IN AN OBJECT

RELATED APPLICATION

This Application claims the benefit, under 35 U.S.C. § 119(e), of U.S. Provisional Application No. 60/486,663, filed Jul. 11, 2003.

TECHNICAL FIELD OF THE INVENTION

This invention relates generally to signal analysis and more particularly to wavelet analysis of one or more acoustic signals to identify one or more anomalies in an object.

BACKGROUND

Previous techniques for analyzing one or more acoustic signals from an acoustic scan of an integrated circuit (IC) package or other object include analyzing the acoustic signals using a Fourier Transform (FT). However, FTs tend to be ineffective at analyzing acoustic signals from an acoustic scan of an object. A drawback of FTs is that, in an FT analysis of a function, the function is assumed to be periodic and to extend infinitely in a time domain. In contrast, an acoustic signal from an acoustic scan of an object is typically a critically damped pulsed signal that, in a time domain, has a rapidly rising leading edge. As a result, FTs cannot accurately represent acoustic signals from an acoustic scan of an object.

SUMMARY OF THE INVENTION

According to the present invention, disadvantages and problems associated with analyzing acoustic signals may be reduced or eliminated.

In one embodiment, a method for wavelet analysis of one or more acoustic signals to identify one or more anomalies in an object includes receiving an acoustic signal from an acoustic scan of an object and calculating a wavelet power spectrum of the acoustic signal. The method also includes accessing a library of one or more reference wavelet power spectra that each correspond to one or more objects that comprise one or more known anomalies and comparing the wavelet power spectrum with one or more reference wavelet power spectra. If the wavelet power spectrum from the acoustic scan corresponds to one or more reference wavelet power spectra, analysis results are communicated indicating that the object under analysis comprises one or more particular known anomalies corresponding to the one or more reference wavelet power spectra that correspond to the wavelet power spectrum. If the wavelet power spectrum does not correspond to one or more reference wavelet power spectra, analysis results are communicated indicating that the object under analysis lacks the one or more known anomalies that the one or more reference wavelet power spectra in the library correspond to.

Particular embodiments of the present invention may provide one or more technical advantages. Particular embodiments may facilitate analysis of acoustic signals from an acoustic scan of an object to more accurately identify one or more anomalies in the object. Particular embodiments may facilitate analysis of acoustic signals from an acoustic scan of an IC package to more accurately identify one or more defects in one or more solder bumps of the IC package. Certain embodiments may provide all, some, or none of these technical advantages. Certain embodiments may provide one or more other technical advantages, one or more of which may be readily apparent to those skilled in the art from the figures, descriptions, and claims herein.

BRIEF DESCRIPTION OF THE DRAWINGS

To provide a more complete understanding of the present invention and the features and advantages thereof, reference is made to the following description, taken in conjunction with the accompanying drawings, in which:

FIG. 4 illustrates another example defect in a solder bump;

FIG. 5 illustrates an example system for analyzing one or more acoustic signals from an acoustic scan of one or more solder bumps of an IC package;

FIG. 6 illustrates an example acoustic signal from an acoustic scan of the defective solder bump illustrated in FIG. 4;

FIG. 7 illustrates an example wavelet transform of the acoustic signal illustrated in FIG. 6;

DESCRIPTION OF EXAMPLE EMBODIMENTS

Figure 1:
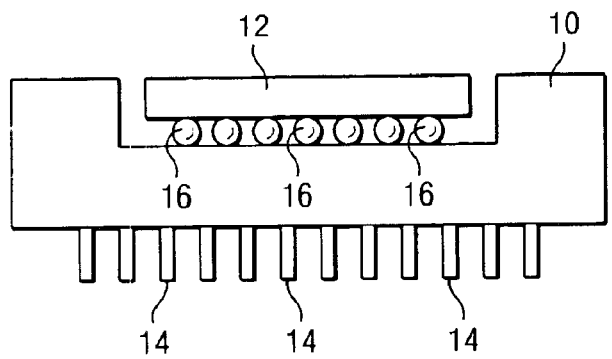
FIG. 1 illustrates an example IC package.

FIG. 1 illustrates an example IC package 10. A die 12 containing an IC may be inserted into IC package 10. IC package 10 may be a ceramic, plastic, or other IC package 10. IC package 10 may include one or more pins 14 for coupling IC package 10 to a circuit board or similar device. Pins 14 may facilitate communication of input signals, output signals, or both to the IC in die 12. IC package 10 may also include one or more solder bumps 16 for coupling die 12 to IC package 10. Die 12 may include one or more lands coupled to the IC in die 12 that each provide an interface between die 12 and a solder bump 16 allowing communication between solder bump 16 and the IC. Portions of an area between IC package 10 and die 12 may include underfill (which may be a polymeric material) that may physically bond IC package 10 to die 12. Although a particular IC package 10 is illustrated and described, the present invention contemplates any suitable IC package 10. In addition, particular embodiments may be used to analyze acoustic scans of objects other than IC packages 10. As an example, particular embodiments may be used to analyze acoustic scans of one or more human tissues.

Figure 2:
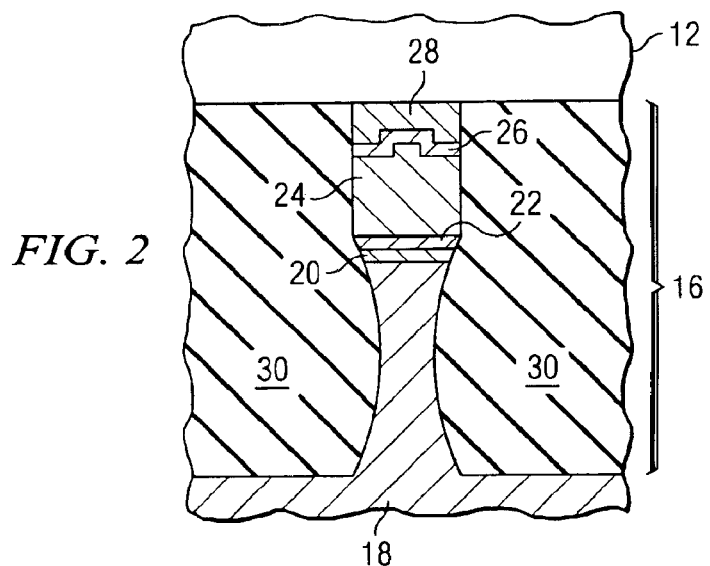
FIG. 2 illustrates an example solder bump.

FIG. 2 illustrates an example solder bump 16. Solder bump 16 is a category 2 solder bump 16 including a tungsten layer 18, a nickel layer 20, a copper layer 22, a solder layer 24, a copper stud 26, and a titanium tungsten (TiW) cap 28. In addition, solder bump 16 may also include an aluminum cap on top of TiW cap 28. Solder layer 24 may include lead- and tin-based or other solder. Solder bump 16 may have a height of approximately several microns. Regions 30 may include underfill between IC package 10 and die 12. When die 12 is inserted into package 10, a land of die 12 that corresponds to solder bump 16 may come into contact with TiW cap 28. Tungsten layer 18 may be coupled to one or more pins 14 of IC package 10. Input to the IC in die 10 may be communicated from a pin 14 to the IC up through tungsten layer 18, nickel layer 20, copper layer 22, solder layer 24, copper stud 26, and TiW cap 28. In addition or as an alternative, output from the IC in die 10 may be communicated from the IC to a pin 14 down through titanium tungsten (TiW) cap 28, copper stud 26, solder layer 24, copper layer 22, nickel layer 20, and tungsten layer 18. As described below, a solder bump 16 may include one or more defects or other anomalies resulting from manufacturing or other processes associated with solder bump 16 or other components of IC package 10. Such defects may adversely affect communication between the IC in die 10 and one or more pins 14. Although a particular solder bump 16 is illustrated, the present invention contemplates any suitable solder bump 16 or other object.

Figure 3:
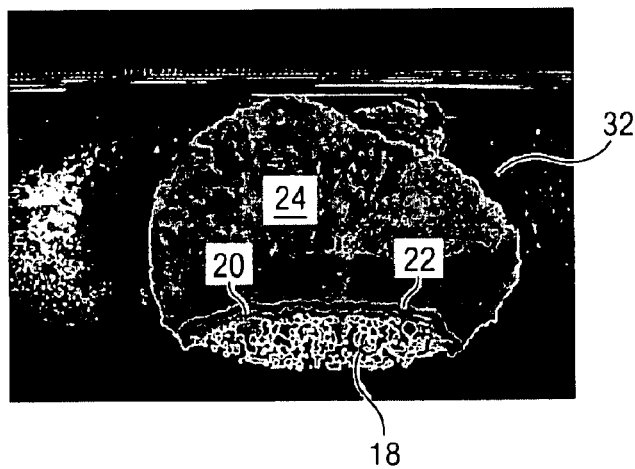
FIG. 3 illustrates an example defect in a solder bump.

FIG. 3 illustrates an example defect 32 in a category 2 solder bump 16. Copper stud 26 of solder bump 16 may be vulnerable to diffusion and, therefore, chemical consumption. Reliability studies indicate that copper stud 26 may, under certain circumstances, dissolve into solder layer 24, which may lead to gradation in the composition of copper stud 26. Copper stud 26 may dissolve to the point that no distinct copper stud 26 exists and the depleted interface between copper stud 16 and TiW cap 28 opens up, which results in an open failure. Defect 32 includes the open interface between copper stud 16 and TiW cap 28. FIG. 4 illustrates another example defect 34 in a category 2 solder bump 16. In solder bump 16, the interface between copper stud 26 and solder layer 24 is open. Defect 34 includes this open interface. As a result of the open interface, a pin corresponding to solder bump 16 cannot communicate input to or output from to the IC in die 12. The open interface may be caused by solder leaking from solder layer 24 into a crevice 36 in the underfill adjacent solder layer 24. Although particular defects 32 and 34 in particular solder bumps 16 are illustrated and described, the present invention contemplates any suitable defect or other anomaly in any suitable solder bump 16 or other object.

FIG. 5 illustrates an example system 40 for analyzing one or more acoustic signals from an acoustic scan of one or more solder bumps 16 of an IC package 10. System 40 includes an acoustic microscope 42, a computer system 44, an analysis module 46, and analysis data 48. Analysis module 46 may be a component of computer system 44 or a device separate from computer system 44. Analysis module 46 may include software, hardware, or both for analyzing acoustic signals. As an example, in particular embodiments, analysis module 46 may include MATLAB or other suitable mathematical analysis tool. Analysis data 48 may include data that may be used to analyze one or more acoustic signals from an acoustic scan of one or more solder bumps 16 of an IC package 10, as described below.

Acoustic microscope 42 may include a C-Mode Scanning Acoustic Microscope (C-SAM) or other acoustic microscope 42. Acoustic microscope 42 may scan one or more solder bumps 16 of IC package 10 with one or more acoustic signals, according to previous techniques. Scanning solder bumps 16 may include directing one or more acoustic signals at solder bumps 16 and recording the acoustic signals after they have reflected off or passed through solder bumps 16. An acoustic signal may include an ultrasound acoustic pulse. After acoustic microscope 42 records the acoustic signals from the acoustic scan, acoustic microscope 42 may (automatically or in response to input from computer system 44 or a user) communicate the acoustic signals to computer system 44 for analysis.

Computer system 44 and analysis module 46 may then analyze the acoustic signals to determine whether a solder bump 16 in IC package 10 includes a defect, as described below. In particular embodiments, computer system 44 may analyze the acoustic signals automatically or in response to input from a user. If solder bump 16 includes a defect, the acoustic signals may be analyzed to identify the defect, as described below. In particular embodiments, this information may be combined with information regarding the location of the defect (including the depth of the defect and the x and y coordinates of the defect relative to IC package 10) to obtain a more complete description of the defect. According to previous techniques, return time (or time-of-flight) information associated with an acoustic signal from an acoustic scan of a defective solder bump 16 of IC package 10 may be used to determine a depth of the defect relative to a surface of IC package 10. Also according to previous techniques, an image generated from the acoustic scan may be used to determine x and y coordinates of the defect relative to IC package 10.

An acoustic signal from an acoustic scan of a solder bump 16 may contain information regarding one or more interfaces encountered by the acoustic signal in solder bump 16. Information in the acoustic signal in a time domain is often difficult to interpret due to reflections from multiple interfaces in solder bump 16 and concomitant convolution effects. In particular embodiments, information in the acoustic signal in a spectral (or frequency) domain may be used to identify one or more defects in solder bump 16. Propagation of an acoustic signal through a multilayered structure is more or less similar, in physical terms, to propagation of a strain wave through the multilayered structure. In the multilayered structure, the strain wave is reflected at every interface between layers having densities that are different from each other. Stresses that accompany propagation of the strain wave may be calculated by solving an applicable wave equation. An approach to solving the wave equation is a transfer-matrix approach using results from potential theory. Propagation of the strain wave is modeled by maintaining continuity of stresses and velocities at interfaces and relating a first potential in a first layer to a second potential in a second layer via a transfer matrix having elements that are dependent on parameters such as material density, wave frequency, incidence angle, and material thickness. The transfer-matrix approach assumes invariance in x and y directions for wave propagation in a z direction.

FT analysis is often used, according to previous techniques, to analyze one or more acoustic signals from an acoustic scan of one or more solder bumps 16. However, there are certain disadvantages associated with using FTs to analyze acoustic signals from an acoustic scan. In FT analysis, only sinusoidal basis functions can be used to reconstruct a signal under analysis. However, since an acoustic signal has a nonstationary power spectrum, nonsinusoidal basis functions may provide a more accurate representation of the acoustic signal than sinusoidal basis functions. In addition, an FT of an acoustic signal assumes the acoustic signal is periodic. However, an acoustic signal from an acoustic scan is typically a pulse. Accordingly, an FT may provide an inaccurate representation of the acoustic signal.

In contrast, in particular embodiments, wavelet analysis is used to analyze one or more acoustic signals from an acoustic scan of a solder bump 16 to identify a defect in solder bumper 16. Unlike FTs, wavelets are not limited to only sinusoidal basis functions. Therefore, in wavelet analysis of an acoustic signal, a basis function for reconstructing the acoustic signal may be selected according to one or more particular characteristics of the acoustic signal. In particular embodiments, a Morlet function is used as a basis function in a wavelet analysis of one or more acoustic signals from an acoustic scan of a solder bump 16. In addition, a wavelet of an acoustic signal does not assume that the acoustic signal is periodic. As a result, wavelet analysis may provide a more accurate representation of the acoustic signal and may provide better time and frequency resolution than FT analysis.

A wavelet scale corresponds to frequency in FT analysis. At different wavelet scales, an acoustic signal may include various signal levels (which may be measured in volts). These signal levels across these wavelet scales constitute a power spectrum of the acoustic signal. The power spectrum of an acoustic signal from an acoustic scan of a solder bump 16 may be used to determine whether solder bump 16 includes one or more defects. In addition, in particular embodiments, a defective solder bump 16 may have a distinctive power spectrum that may be used to identify the defect. As an example, consider a first power spectrum corresponding to a first solder bump 16 being examined. The first power spectrum may be compared with one or more second power spectra from a library of power spectra corresponding to one or more second nondefective solder bumps 16 and power spectra corresponding to one or more second defective solder bumps 16 with particular defects. Analysis data 48 may include this library of power spectra. If the first power spectrum corresponds to one or more second power spectra corresponding to one or more second nondefective solder bumps 16, it may be concluded that first solder bump 16 is nondefective. If, on the other hand, the first power spectrum corresponds to one or more second power spectra corresponding to one or more second defective solder bumps 16 with a particular defect, it may be concluded that first solder bump 16 includes that particular defect. In particular embodiments, one or more suitable statistical analysis techniques may be used to determine whether the first power spectrum corresponds to one or more second power spectra. One or more such techniques may estimate a probability that a peak from a wavelet power spectrum is significant with respect to a background spectrum.

FIG. 6 illustrates an example acoustic signal 50 from an acoustic scan of defective solder bump 16 illustrated in FIG. 4, and FIG. 7 illustrates an example wavelet transform 52 of acoustic signal 50. The y axis of FIG. 6 includes a range of voltages measured in mV. The x axis of FIG. 6 includes a range of time measured in $10^{-7}$ seconds. The y axis of FIG. 7 includes a range of wavelet scales. The x axis of FIG. 7 includes a range of five hundred samples from acoustic signal 50 at certain times. The x axes of FIGS. 6 and 7 may correspond to each other such that sample fifty corresponds to −0.2 microseconds, sample two hundred fifty corresponds to 0 microseconds, sample three hundred fifty corresponds to 0.1 microsecond, and so on. A Morlet basis function has been used to compute wavelet coefficients of wavelet transform 52, which are shown as a function of wavelet scale. Wavelet coefficients at smaller wavelet scales indicate a similarity between the Morlet basis function and acoustic signal 50. In addition, wavelet coefficients across multiple wavelet scales in the low scale regime display similar structure indicating fractal character of acoustic signal 50.

In wavelet transform 52, a brightness of a point at an intersection of a sample and a wavelet scale indicates a wavelet coefficient computed according to a Morlet basis function of that sample at that wavelet scale. Consider a first point in wavelet transform 52 that corresponds to a first sample at a first wavelet scale and a second point in wavelet transform 52 that corresponds to a second sample at a second wavelet scale. A first brightness at the first point corresponds to a first computed wavelet coefficient of the first sample at the first wavelet scale, and a second brightness at the second point corresponds to a second computed wavelet coefficient of the second sample at the second wavelet scale. If the first brightness is greater than the second brightness, the first computed wavelet coefficient has a magnitude that is greater than a magnitude of the second computed wavelet coefficient.

Figure 8:
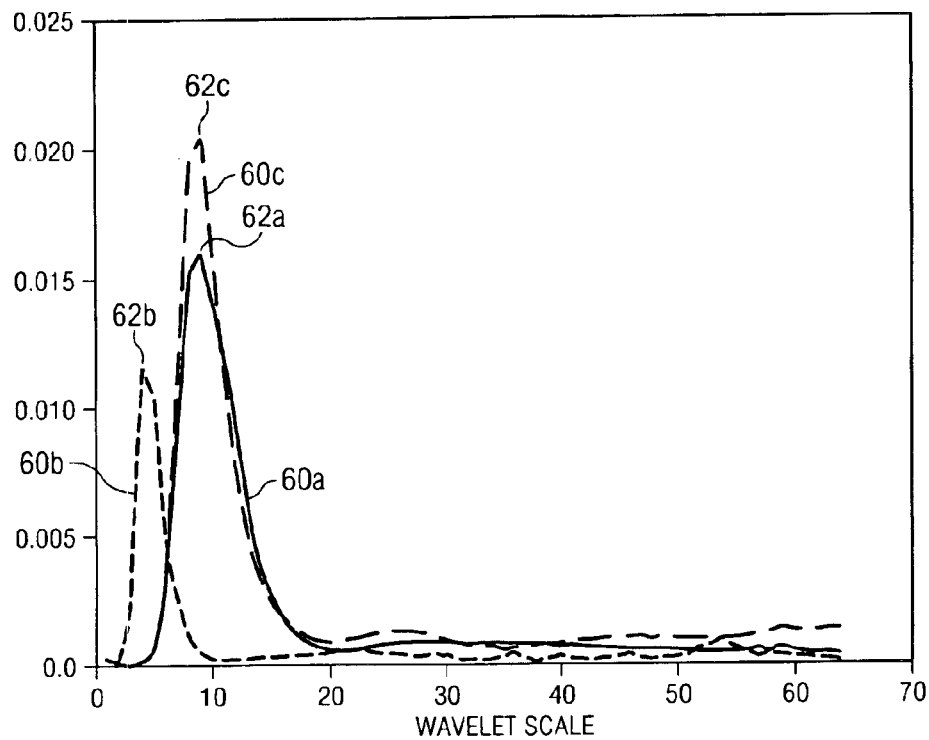
FIG. 8 illustrates a first example wavelet power spectrum of a nondefective solder bump, a second example wavelet power spectrum of the defective solder bump illustrated in FIG. 3, and a third example wavelet power spectrum of the defective solder bump illustrated in FIG. 4.

FIG. 8 illustrates example wavelet power spectra 60 of acoustic signals from acoustic scans of solder bumps 16. Wavelet power spectrum 60a corresponds to a nondefective solder bump 16, wavelet power spectrum 60b corresponds to defective solder bump 16 illustrated in FIG. 3, and wavelet power spectrum 60c corresponds to defective solder bump 16 illustrated in FIG. 4. Power spectra 60 may be more or less conceptually analogous to a Fourier power spectrum. The x axis of FIG. 8 includes a range of wavelet scales, and they axis of FIG. 8 includes a range of averages of squared wavelet coefficients across all samples at a certain wavelet scale. As an example, wavelet power spectrum 60b includes a point corresponding to approximately 7.0 along the x axis and approximately 0.01 along the y axis. This indicates that, in power spectrum 60b, the average of the squares of each computed wavelet coefficient of each sample at a wavelet scale of seven is 0.01. In keeping with transfer-matrix calculation, wavelet power spectrum 60b has a peak 62 at a lower scale (or lower pseudofrequency) than wavelet power spectrum 60c. The air interface of defect 34 (illustrated in FIG. 4) is, at least on average, deeper than the air interface of defect 32 (illustrated in FIG. 3).

In particular embodiments, one or more aspects of a wavelet power spectrum 60 may indicate whether a corresponding solder bump 16 is defective. As an example, a position of peak 62a with respect to the x axis, y axis, or both may indicate that corresponding solder bump 16 is nondefective. As another example, a position of peak 62b with respect to the x axis, y axis, or both may indicate that corresponding solder bump 16 is defective. In addition or as an alternative, in particular embodiments, one or more aspects of a wavelet power spectrum 60 may, if a corresponding solder bump 16 is defective, identify the defect in solder bump 16. As an example, a position of peak 62b with respect to the x axis, y axis, or both may indicate that defect 32 includes an open interface between copper stud 16 and TiW cap 28 in solder bump 16. In addition, in particular embodiments, the position of peak 62b may further indicate the size (with respect to one or more dimensions) of the opening in the interface. In addition, in particular embodiments, the position of peak 62b may even further indicate what the contents (which could be air, underfill, another material, or nothing) of the opening in the interface.

Figure 9:
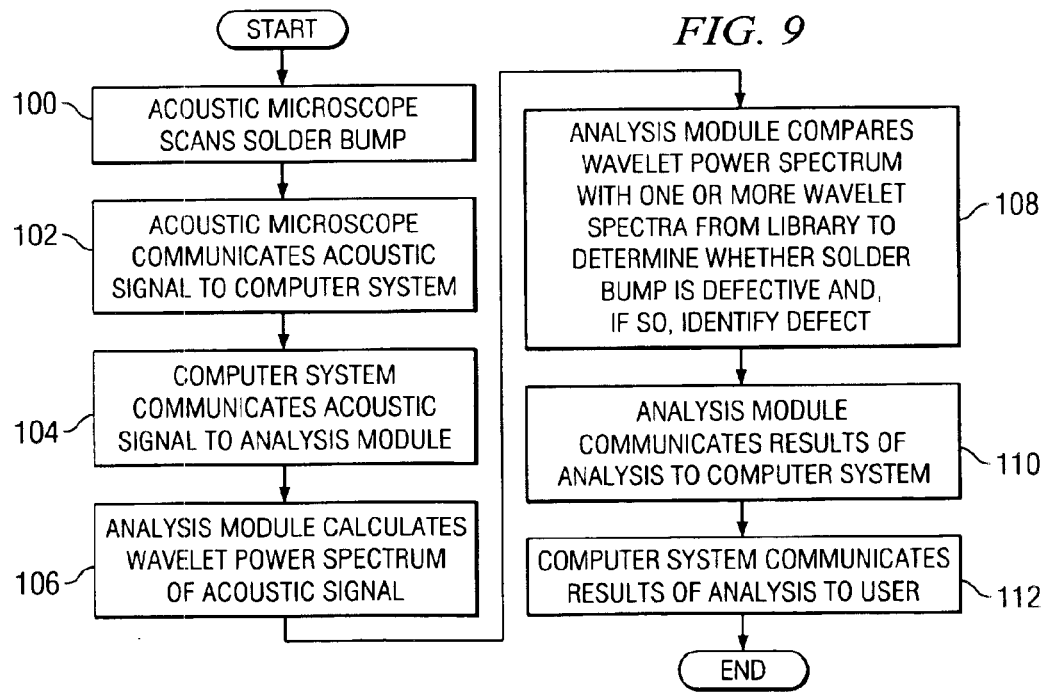
FIG. 9 illustrates an example method for wavelet analysis of one or more acoustic signals to identify one or more anomalies in an object.

FIG. 9 illustrates an example method for wavelet analysis of one or more acoustic signals to identify one or more anomalies in an object. The method begins at step 100, where acoustic microscope 42 scans a solder bump 16 with an acoustic signal. At step 102, acoustic microscope 42 communicates the acoustic signal from the acoustic scan of solder bump 16 to computer system 44. At step 104, computer system 44 communicates the acoustic signal to analysis module 46 for analysis. At step 106, analysis module 46 calculates a wavelet power spectrum of the acoustic signal, as described above. At step 108, analysis module 46 compares the wavelet power spectrum of the acoustic signal with one or more wavelet power spectra from a library of wavelet power spectra to determine whether solder bump 16 is defective and, if so, identify the defect. Analysis data 48 may include the library of wavelet power spectra. In particular embodiments, wavelet power spectra in the library may each correspond to one or more solder bumps 16 known to be defective or nondefective.

In addition, a wavelet power spectrum in the library that corresponds to one or more defective solder bumps 16 may correspond to one or more known defects. If the wavelet power spectrum of the acoustic signal from the acoustic scan of solder bump 16 more or less matches a wavelet power spectrum in the library, it may be concluded that solder bump 16 is either defective or nondefective, according to the matching wavelet power spectrum in the library. In addition, if the matching wavelet power spectrum in the library corresponds to one or more defective solder bumps 16 with one or more certain known defects, it may be concluded that solder bump 16 includes the one or more certain known defects. In particular embodiments, one or more wavelet power spectra in the library each include a combination (such as an average) of two or more wavelet power spectra corresponding to two or more solder bumps 16 known to be defective or nondefective. In particular embodiments, one or more suitable statistical analysis techniques may be used to determine whether the wavelet power spectrum of the acoustic signal from the acoustic scan corresponds to one or more power spectra in the library. At step 110, analysis module 46 communicates results of the analysis to computer system 44. At step 112, computer system 44 communicates the results to one or more users, at which point the method ends.

Although the present invention has been described with several embodiments, myriad changes, variations, alterations, transformations, and modifications may be suggested to one skilled in the art, and it is intended that the present invention encompass such changes, variations, alterations, transformations, and modifications as fall within the scope of the appended claims. The present invention is not intended to be limited, in any way, by any statement in the specification that is not reflected in the claims.

What is claimed is:

1. A system for wavelet analysis of one or more acoustic signals to identify one or more anomalies in an object, the system comprising:
    a library of one or more reference wavelet power spectra that each correspond to one or more objects that comprise one or more known anomalies; and
    an analysis module operable to:
        receive an acoustic signal from an acoustic scan of an object;
        calculate a wavelet power spectrum of the acoustic signal;
        access the library;
        compare the wavelet power spectrum with one or more reference wavelet power spectra;
        if the wavelet power spectrum from the acoustic scan corresponds to one or more reference wavelet power spectra, communicate analysis results indicating that the object under analysis comprises one or more particular known anomalies corresponding to the one or more reference wavelet power spectra that correspond to the wavelet power spectrum; and
        if the wavelet power spectrum does not correspond to one or more reference wavelet power spectra, communicate analysis results indicating that the object under analysis lacks the one or more known anomalies that the one or more reference wavelet power spectra in the library correspond to.

2. The system of claim 1, wherein a wavelet transform is used to calculate the wavelet power spectrum of the acoustic signal from the acoustic scan of the object.

3. The system of claim 1, wherein a Morlet basis function is used to calculate the wavelet power spectrum of the acoustic signal from the acoustic scan of the object.

4. The system of claim 1, wherein one or more locations of the one or more anomalies with respect to the object are determined according to the acoustic scan of the object.

5. The system of claim 1, wherein a C-Mode Scanning Acoustic Microscope (C-SAM) is used to take the acoustic scan of the object.

6. The system of claim 1, wherein the object is a solder bump of an integrated circuit (IC) package.

7. A method for wavelet analysis of one or more acoustic signals to identify one or more anomalies in an object, the method comprising:
    receiving an acoustic signal from an acoustic scan of an object;
    calculating a wavelet power spectrum of the acoustic signal;
    accessing a library of one or more reference wavelet power spectra that each correspond to one or more objects that comprise one or more known anomalies;
    comparing the wavelet power spectrum with one or more reference wavelet power spectra;
    if the wavelet power spectrum from the acoustic scan corresponds to one or more reference wavelet power spectra, communicating analysis results indicating that the object under analysis comprises one or more particular known anomalies corresponding to the one or more reference wavelet power spectra that correspond to the wavelet power spectrum; and
    if the wavelet power spectrum does not correspond to one or more reference wavelet power spectra, communicating analysis results indicating that the object under analysis lacks the one or more known anomalies that the one or more reference wavelet power spectra in the library correspond to.

8. The method of claim 7, wherein a wavelet transform is used to calculate the wavelet power spectrum of the acoustic signal from the acoustic scan of the object.

9. The method of claim 7, wherein a Morlet basis function is used to calculate the wavelet power spectrum of the acoustic signal from the acoustic scan of the object.

10. The method of claim 7, wherein one or more locations of the one or more anomalies with respect to the object are determined according to the acoustic scan of the object.

11. The method of claim 7, wherein a C-Mode Scanning Acoustic Microscope (C-SAM) is used to take the acoustic scan of the object.

12. The method of claim 7, wherein the object is a solder bump of an integrated circuit (IC) package.

13. Software for wavelet analysis of one or more acoustic signals to identify one or more anomalies in an object, the software embodied in computer-readable media and when executed operable to:
    receive an acoustic signal from an acoustic scan of an object;
    calculate a wavelet power spectrum of the acoustic signal;
    access a library of one or more reference wavelet power spectra that each correspond to one or more objects that comprise one or more known anomalies;
    compare the wavelet power spectrum with one or more reference wavelet power spectra;

if the wavelet power spectrum from the acoustic scan corresponds to one or more reference wavelet power spectra, communicate analysis results indicating that the object under analysis comprises one or more particular known anomalies corresponding to the one or more reference wavelet power spectra that correspond to the wavelet power spectrum; and if the wavelet power spectrum does not correspond to one or more reference wavelet power spectra, communicate analysis results indicating that the object under analysis lacks the one or more known anomalies that the one or more reference wavelet power spectra in the library correspond to.

14. The software of claim 13, wherein a wavelet transform is used to calculate the wavelet power spectrum of the acoustic signal from the acoustic scan of the object.

15. The software of claim 13, wherein one or more locations of the one or more anomalies with respect to the object are determined according to the acoustic scan of the object.

16. The software of claim 13, wherein a C-Mode Scanning Acoustic Microscope (C-SAM) is used to take the acoustic scan of the object.

17. The software of claim 13, wherein the object is a solder bump of an integrated circuit (IC) package.

18. A system for wavelet analysis of one or more acoustic signals to identify one or more anomalies in an object, the system comprising:

means for receiving an acoustic signal from an acoustic scan of an object;

means for calculating a wavelet power spectrum of the acoustic signal;

means for accessing a library of one or more reference wavelet power spectra that each correspond to one or more objects that comprise one or more known anomalies;

means for comparing the wavelet power spectrum with one or more reference wavelet power spectra;

means for, if the wavelet power spectrum from the acoustic scan corresponds to one or more reference wavelet power spectra, communicating analysis results indicating that the object under analysis comprises one or more particular known anomalies corresponding to the one or more reference wavelet power spectra that correspond to the wavelet power spectrum; and means for, if the wavelet power spectrum does not correspond to one or more reference wavelet power spectra, communicating analysis results indicating that the object under analysis lacks the one or more known anomalies that the one or more reference wavelet power spectra in the library correspond to.

19. A system for wavelet analysis of one or more acoustic signals to identify one or more defects in a solder bump of an integrated circuit (IC) package, the system comprising:

a library of one or more reference wavelet power spectra that each correspond to one or more solder bumps that comprise one or more known defects; and an analysis module operable to:
receive an acoustic signal from an acoustic scan of a solder bump;
calculate a wavelet power spectrum of the acoustic signal using a Morlet basis function;
access the library;
compare the wavelet power spectrum with one or more reference wavelet power spectra;
if the wavelet power spectrum from the acoustic scan corresponds to one or more reference wavelet power spectra, communicate analysis results indicating that the solder bump under analysis comprises one or more particular known defects corresponding to the one or more reference wavelet power spectra that correspond to the wavelet power spectrum; and
if the wavelet power spectrum does not correspond to one or more reference wavelet power spectra, communicate analysis results indicating that the solder bump under analysis lacks the one or more known defects that the one or more reference wavelet power spectra in the library correspond to.

* * * * *